United States Patent
Chaintreuil

(10) Patent No.: US 10,813,613 B2
(45) Date of Patent: Oct. 27, 2020

(54) METHOD AND SYSTEM FOR CHARACTERISING A BONE TISSUE

(71) Applicant: MEDIMAPS GROUP SA, Plan-les-Ouates, Geneva (CH)

(72) Inventor: Jean Chaintreuil

(73) Assignee: MEDIMAPS GROUP SA, Plan-les-Ouates, Geneve (CH)

( * ) Notice: Subject to any disclaimer, the term of this patent is extended or adjusted under 35 U.S.C. 154(b) by 1339 days.

(21) Appl. No.: 14/782,167

(22) PCT Filed: Mar. 31, 2014

(86) PCT No.: PCT/EP2014/056486
§ 371 (c)(1),
(2) Date: Oct. 2, 2015

(87) PCT Pub. No.: WO2014/161827
PCT Pub. Date: Oct. 9, 2014

(65) Prior Publication Data
US 2016/0029988 A1    Feb. 4, 2016

(30) Foreign Application Priority Data

Apr. 3, 2013   (FR) ...................................... 13 53003

(51) Int. Cl.
*A61B 5/05*    (2006.01)
*A61B 6/00*    (2006.01)
*G06T 7/00*    (2017.01)

(52) U.S. Cl.
CPC .............. *A61B 6/505* (2013.01); *A61B 6/469* (2013.01); *A61B 6/5217* (2013.01); *A61B 6/583* (2013.01);
(Continued)

(58) Field of Classification Search
CPC . G06T 2207/10116; G06T 2207/10081; G06T 2207/30008; G06T 2207/30004;
(Continued)

(56) References Cited

U.S. PATENT DOCUMENTS

| 6,205,348 B1 | 3/2001 | Giger et al. |
| 2004/0114726 A1 | 6/2004 | Lee et al. |

(Continued)

FOREIGN PATENT DOCUMENTS

FR  2960762 A1   12/2011

OTHER PUBLICATIONS

French Search Report from French Patent Application No. 1353003, dated Sep. 5, 2013.
(Continued)

*Primary Examiner* — Elmer M Chao
(74) *Attorney, Agent, or Firm* — Greer, Burns & Crain, Ltd.

(57) ABSTRACT

A method is provided for the characterization of a bone tissue with an imaging device, including:
acquisition of at least one bone tissue grey scale image at a measurement value ($MAS_1$), of an emission parameter relating to emitted radiation,
image analysis measurement:
of a measured value ($SD_1$), of a standard deviation of the grey levels;
of a measured value ($GLA_1$) of a mean grey level; and
of a measured value, of a characterization parameter ($H_1$) of the bone tissue;
target calibration, of the measured value ($H_1$) with respect to a target value ($GLA_{target}$), of a predetermined mean grey level for the sensor, the calibration producing a target value ($H_{target}$);
fixed calibration of the measured value ($SD_1$) with respect to a fixed value ($MAS_{fixed}$), of the predetermined emission parameter; and
(Continued)

determination of a corrected value ($H_{corrected}$), of the value of the characterization parameter.

9 Claims, 3 Drawing Sheets

(52) U.S. Cl.
CPC .. *G06T 7/0014* (2013.01); *G06T 2207/10116* (2013.01); *G06T 2207/20076* (2013.01); *G06T 2207/30008* (2013.01)

(58) Field of Classification Search
CPC .... G06T 11/005; G06T 11/006; G06T 11/003; A61B 6/5211; A61B 6/5258; A61B 6/505; A61B 6/032; A61B 5/4504; A61B 5/4509; A61B 2090/376; A61B 2090/3762; G01N 23/046; G01N 23/083; G01N 2800/108; G03B 42/02; G16H 50/20

See application file for complete search history.

(56) References Cited

U.S. PATENT DOCUMENTS

2006/0062442 A1     3/2006   Arnaud et al.
2007/0047794 A1     3/2007   Lang et al.

OTHER PUBLICATIONS

International Search Report from International Application No. PCT/EP2014/056486, dated May 27, 2014.

METHOD AND SYSTEM FOR CHARACTERISING A BONE TISSUE

BACKGROUND

The present invention relates to a method for characterizing a bone tissue. It also relates to a system implementing such a method.

The field of the invention is the medical field and more particularly the field of the investigation of bone tissues with imaging devices comprising an emitter of uncharged particles and utilizing a radiation sensor. The invention applies more particularly to the field of high-precision medical imaging and to the investigation of bone texture.

STATE OF THE ART

Currently, numerous devices exist for imaging bone tissues. These devices comprise a source of uncharged particles provided in order to emit radiation and optionally a receiver provided with a sensor. The bone tissue is positioned between the emitter and the receiver.

The method implemented in these devices comprises emission of radiation of uncharged particles which strike the bone tissue. The uncharged particles pass through the medium investigated to a greater or lesser extent, depending on its density. Attenuation is greater in an osseous medium than in the soft tissues.

The image obtained by these methods is a grey scale image, and the grey level at a point of the obtained image depends on the quantity of particles striking the sensor at this point. The grey scale image is then analyzed and processed in order to determine the value of one or more parameters relating to the osseous medium, also known in the present application as the "characterization parameter". Such a characterization parameter can be for example the texture parameter H, also known as the Hurst parameter.

Correct characterization of the bone tissues, and in particular of the bones, involves the reduction, or even elimination, of the effects on the image produced of the soft tissues surrounding the bone. In fact, a major difficulty in the characterization of bones is to obtain a result which is independent of the quantity and type of soft tissues surrounding the bone to be characterized, which introduce interference into the image and thus into the determination of a characterization parameter.

Furthermore, the applicant has noted that the uncharged particles which reach the sensor at a given point comprise on the one hand, incident particles originating directly from the emitter and having passed through the bone tissue and the soft tissues opposite this given point, and on the other hand, uncharged particles scattered by other parts of the bone tissue and soft tissues which are not situated opposite the given point. These scattered uncharged particles also introduce interference which is found on the grey scale image and thus in the value of a characterization parameter.

The current methods and systems for characterization of bone tissues produce a characterization of the bone tissue without taking account of this interference, giving approximate results which in some cases can be aberrant.

A purpose of the invention is to overcome the aforementioned drawbacks.

Another purpose of the invention is to propose a method and system for characterization of a bone tissue making it possible to reduce, or even eliminate, interference caused by the soft tissues and/or by the scattered radiation during the characterization of the bone tissues.

Another purpose of the present invention is to propose a method and system for the characterization of a bone tissue making it possible to determine the value of a characterization parameter independently of the device used, in particular of the sensor used, and/or the conditions of characterization.

Finally, another purpose of the invention is to propose a method and system for the characterization of a bone tissue producing a more precise characterization than the current methods and systems.

SUMMARY

The invention proposes to achieve at least one of these aims by a method for the characterization of a bone tissue with an imaging device comprising a radiation emitter and utilizing a radiation sensor, said method being characterized in that it comprises the following steps:
  acquisition of at least one grey scale image of said bone tissue with said imaging device at a value ($MAS_1$), known as measurement value, of an emission parameter relating to the emitted radiation,
  measurement, by analysis of said image:
    of a value ($SD_1$), known as measured value, of a standard deviation of the grey levels,
    of a value ($GLA_1$), known as measured value, of a mean grey level, and
    of a value, known as measured value, of a characterization parameter ($H_1$) of said bone tissue;
  calibration, known as target calibration, of said measured value ($H_1$) of the characterization parameter with respect to a value ($GLA_{target}$) known as target value, of a predetermined mean grey level for said sensor, said calibration producing a value ($H_{target}$), known as target value, of said characterization parameter,
  calibration, known as fixed calibration, of said measured value ($SD_1$) of the standard deviation of the grey levels with respect to a value ($MAS_{fixed}$), known as fixed value, of the predetermined emission parameter, said calibration producing a value, known as fixed value ($SD_{fixed}$) of the standard deviation of the grey levels, and
  determination of a value ($H_{corrected}$) known as corrected value, of the value of said characterization parameter, as a function of said target value ($H_{target}$) of said characterization value, of said fixed value ($SD_{fixed}$), and of a target value ($SD_{target}$) of the standard deviation of the grey levels.

The method according to the invention thus proposes to carry out a characterization of a tissue firstly by measurement of the value of a characterization parameter, then by correction of the measured value.

The correction of the measured value comprises a step of target calibration making it possible to reference the measured value with respect to a mean grey level target value for the sensor used, and thus to correct the measurement produced with respect to the sensor. The target value ($GLA_{target}$) of the mean grey level allows the measurement produced to be brought within an operating range recommended by the manufacturer. In fact, an image which is too "dark" indicates an emission level that is too low, and an image that is too "light" indicates an emission level that is too high, while neither of these images presents sufficient contrast to determine the characterization parameter correctly.

The correction also comprises a fixed calibration step making it possible to reference the measurement produced with respect to a previously chosen fixed value of the emission parameter relating to the quantity of particles emitted, making it possible to correct the measurement produced with respect to the conditions of measurement.

The applicant discovered that the quantity of photons scattered in a grey scale image is a function of values of the dispersion of the grey levels in this image. The applicant also discovered, surprisingly, that the interference introduced by the scattered photons in the determination of a characterization parameter can be corrected by taking account, on the one hand, of two values relating to the grey levels for two values for one and the same emission parameter of the emitter, and on the other hand, a constant which can be previously determined empirically.

Implementation of the method requires the acquisition of a single image at a measurement value of an emission parameter of the emitter and the measurement of a value relating to the grey levels.

Thus, the method according to the invention makes it possible to carry out a characterization of a bone tissue, for example of bone texture, while restricting or even eliminating interference caused by the scattered radiation, the type of sensor used and the conditions under which the grey scale image is taken.

As the amount and the nature of the soft tissue surrounding the bone is one of the causes, or even the main cause, of the scattered radiation, the method according to the invention also makes it possible to eliminate interference from the soft tissue in the characterization of a bone tissue.

Advantageously, the grey scale image can be produced by a digital detector. The grey scale image can alternatively be produced using analogue means or on X-ray film. In the latter case, the method according to the invention also comprises a step of digitization of such an analogue image, produced on X-ray film for example.

Advantageously, the target value ($GLA_{target}$) of the mean grey level is chosen as a function of the sensor, and more particularly of the grey scale range that can be obtained by the sensor used.

More particularly, the target value ($GLA_{target}$) of the mean grey level chosen for a given sensor is approximately, in particular equal to, the median grey level value for the given sensor.

For example, for a sensor trade marked Hamamatsu® offering 4096 grey levels, the chosen $GLA_{target}$ value can be 2000.

Advantageously, the fixed value ($MAS_{fixed}$) of the emission parameter can be chosen close to the lower limit of the emission parameter values observed in clinical imaging for a sensor model. For example, the fixed value ($MAS_{fixed}$) of the chosen emission parameter can be 10 mAs, while the measurement value ($MAS_1$) used for the acquisition of the image can be 15 mAs.

Advantageously, the target calibration step can also comprise a determination of the target value ($SD_{target}$) of the standard deviation of the grey levels as a function of the measurement value ($MAS_1$) of the emission parameter and of a predetermined target value ($MAS_{target}$) of said emission parameter.

The target value ($SD_{target}$) of the standard deviation of the grey levels can advantageously be determined according to the following relationship:

$$SD_{target} = SD_1\left(\frac{MAS_{target}}{MAS_1}\right) \quad (1)$$

with
$SD_{target}$ the target value of the standard deviation of the grey levels,
$SD_1$ the measured value of the standard deviation of the grey levels,
$MAS_{target}$ a target value of the emission parameter, and
$MAS_1$ the measurement value of the emission parameter.

Prior to the determination of the target value ($SD_{target}$) of the standard deviation of the grey levels, the calibration step can comprise determination of the target value ($MAS_{target}$) of the emission parameter as a function of the measurement value of the emission parameter ($MAS_1$), of the measured value ($GLA_1$) of the mean grey level, and of the predetermined target value ($GLA_{target}$) of the mean grey level for the sensor used.

The target value ($MAS_{target}$) of the emission parameter can advantageously be determined according to the following relationship:

$$MAS_{target} = MAS_1\left(\frac{GLA_{target} - ct}{GLA_1 - ct}\right) \quad (2)$$

with:
$MAS_{target}$ the target value of the emission parameter,
$MAS_1$ the measured value of the emission parameter,
$GLA_{target}$ the mean grey level target value,
$GLA_1$ the measured value of the mean grey level, and
ct a constant, the value of which is close to the maximum number of grey levels available for a detector model, plus or minus a specific adjustment of the detector.

The constant "ct" can be previously determined empirically with accuracy, via a series of measurements.

Advantageously, the fixed value ($SD_{fixed}$) of the standard deviation of the grey levels can be determined according to the following relationship:

$$SD_{fixed} = SD_1\left(\frac{MAS_{fixed}}{MAS_1}\right) \quad (3)$$

with:
$SD_{fixed}$ the fixed value of the standard deviation of the grey levels,
$SD_1$ the measured value of the standard deviation of the grey levels,
$MAS_{fixed}$ the fixed value of the emission parameter, and
$MAS_1$ the measurement value of the emission parameter.

The grey scale image is acquired around a previously identified region, known as region of interest.

The identification of the region of interest can be carried out by taking a prior image, in particular in grey scale, and by identifying, on this prior image, at least one anatomical marker.

According to a preferred embodiment of the invention, the characterization parameter of the bone tissue can be the parameter H, also known as the Hurst parameter.

In a particular embodiment, the value of H can be derived from the fractional Brownian motion defined in the frequency domain by the following stochastic integral:

$$B_H(t) = \frac{1}{2\pi}\int_{-\infty}^{+\infty}\frac{1}{(i\omega)^{H+1/2}}(e^{it\omega} - 1)dB(\omega)$$

for 0<H<1, B(ω) being the complex Brownian motion. As H cannot be deduced from this integral, it is determined by the maximum likelihood estimation (MLE) method.

The maximum likelihood estimation of H can be produced on the basis of the increment vector (fractional Gaussian noise (fGn)) of the signal, $G_1$, ($G_1(t)=B_H(t+1)-B_H(t)$). In fact, the fGn is stationary Gaussian centred, and its probability density, parametered via H and C, is written:

$$P(G_1; H, C) = \frac{1}{(2\pi)^{(\frac{N}{2})}|R|^{\frac{1}{2}}} \exp\left(-\frac{1}{2}G_1^T R^{-1} G_1\right),$$

where R is the autocorrelation matrix of $G_1$ which depends on H and on the constant C.

The maximum likelihood estimation corresponds to the value of H for which this probability is maximal. The logarithm of the maximum likelihood function allows this expression to be simplified:

$$\mathrm{Log}(P(G_1; H, C)) = -\frac{N}{2}\mathrm{Log}(2\pi) - \frac{1}{2}\mathrm{Log}(|R|) - \frac{1}{2}G_1^T R^{-1} G_1.$$

R can be decomposed into C R'. Under these conditions the above equation becomes:

$$\mathrm{Log}(P(G_1; H, C)) = -\frac{N}{2}\mathrm{Log}(2\pi) - \frac{N}{2}\mathrm{Log}(C) - \frac{1}{2}\mathrm{Log}(|R'|) - \frac{1}{2C}G_1^T R'^{-1} G_1.$$

The maximum of this expression with respect to C can be found by cancelling the corresponding partial derivative. The following is then obtained:

$$\frac{\partial \mathrm{Log}(P(G_1; H, C))}{\partial C} = 0\_C = \frac{G_1^T R'^{-1} G_1}{N}$$

By substituting the thus obtained value of C in the equation and disregarding the constant terms, the function to be maximized is obtained:

$$\mathrm{Log}(P(G_1; H)) = -N\mathrm{Ln}\left(\frac{G_1^T R'^{-1} G_1}{N}\right) - \mathrm{Ln}\_R'\_.$$

As the form of the estimator is not explicit, the probability maximum must be calculated by a numerical method. This is found using the golden ratio method which consists of finding the maximum within a bounded interval (in this case [0, 1]) and makes it possible to find the maximum at the end of a fixed number of iterations for a given precision. At each iteration the search interval is reduced by a factor equal to the golden ratio. Calculation of the determinant and of the inverse of the autocorrelation matrix is carried out using the Levinson algorithm.

In the event that the characterization parameter of the bone tissue is H, the target value ($H_{target}$) of the characterization parameter can advantageously be determined according to the following relationship:

$$H_{target} = H_1 + ((GLA_{target} - GLA_1) \cdot ((a \cdot 10^{-b}) - (c \cdot 10^{-d} \cdot (GLA_{target} + GLA_1)))) \quad (4)$$

with:
$H_{target}$ the target value of the parameter H,
$H_1$ the measured value of the parameter H,
$GLA_{target}$ the mean grey level target value,
$GLA_1$ the measured value of the mean grey level, and
"a", "b", "c" and "d", constant values, specific to the detector model, determined by quadratic regression of H as a function of GLA on the calibration phantoms.

In addition, the corrected value ($H_{corrected}$) of the parameter H can advantageously be determined according to the following relationship:

$$H_{corrected} = H_{target} + e\left(\frac{1}{SD_{fixed}} - \frac{1}{SD_{target}}\right) \quad (5)$$

with:
$H_{corrected}$ the corrected value of the parameter H,
$H_{target}$ the target value of the parameter H,
$SD_{target}$ the target value of the grey level standard deviation,
$SD_{fixed}$ the fixed value of the standard deviation of the grey levels, and
"e" a constant value.

In each of the relationships given in the present application, at least one constant value is a value previously determined empirically for a given sensor and for a given characterization parameter, optionally for a given supply voltage of the emitter and/or a tissue to be characterized, or also an anatomical zone to the characterized.

Each constant value can be determined by carrying out a plurality of measurements with subjects or objects for which the characterization parameter is known.

For example, the value of the constant "e" can be determined during a phase comprising the following steps:
measurements of the characterization parameter, for example the parameter H, for objects made of plastic having a thickness 0, 0.5 cm, 1 cm, 2 cm, 3 cm and 4 cm, or of some of them.
for each measurement i, determining the slope "$e_i$" of the curve linking $H_{corrected, i}$ to the quantity $$\left(\frac{1}{SD_{fixed}} - \frac{1}{SD_{target}}\right),$$

and
mean of the values of "$e_i$".

For a sensor trade marked Hamamatsu® offering 4096 grey levels and for imaging the calcaneum, e=9.6.

According to another particular example, the characterization parameter can be the density of bone tissues.

According to another aspect of the invention, a system is proposed comprising means arranged and programmed for implementing the steps of the method according to the invention.

Such a system comprises:
a medical imaging device comprising an emitter and utilizing a receiver,
a control module,
processing means, which includes a processing module or a processor, for processing grey scale images in order to determine the above-described different measurements, and calculation means arranged in order to determine the above-described different values, namely corrected, fixed and target values.

The control module can be programmed to communicate with and to control the processing means, the calculation means and the emitter.

The control module, the processing module and the calculation means can be at least partially incorporated into the medical imaging device.

Broadly defined, the present invention makes use of the relationship for a given object between the proportion of scattered radiation in the dose received by the detector and the standard deviation of the grey levels over a grey scale image.

Consequently, any characterization parameter of an object the measurement of which is sensitive to scattered radiation could be determined/corrected according to the present invention.

BRIEF DESCRIPTION OF THE DRAWINGS

Other characteristics and advantages of the invention will become apparent on examination of the detailed description of an embodiment which is in no way limitative, and the attached drawings in which.

It is well understood that the embodiments that will be described hereinafter are in no way limitative. Variants of the invention can in particular be imagined, comprising only a selection of features described hereinafter in isolation from the other features described, if this selection of features is sufficient to confer a technical advantage or to differentiate the invention with respect to the state of the prior art. This selection comprises at least one feature, preferably functional without structural details, or with only a part of the structural details if this part alone is sufficient to confer a technical advantage or to differentiate the invention with respect to the state of the prior art.

DETAILED DESCRIPTION

Figure 1:
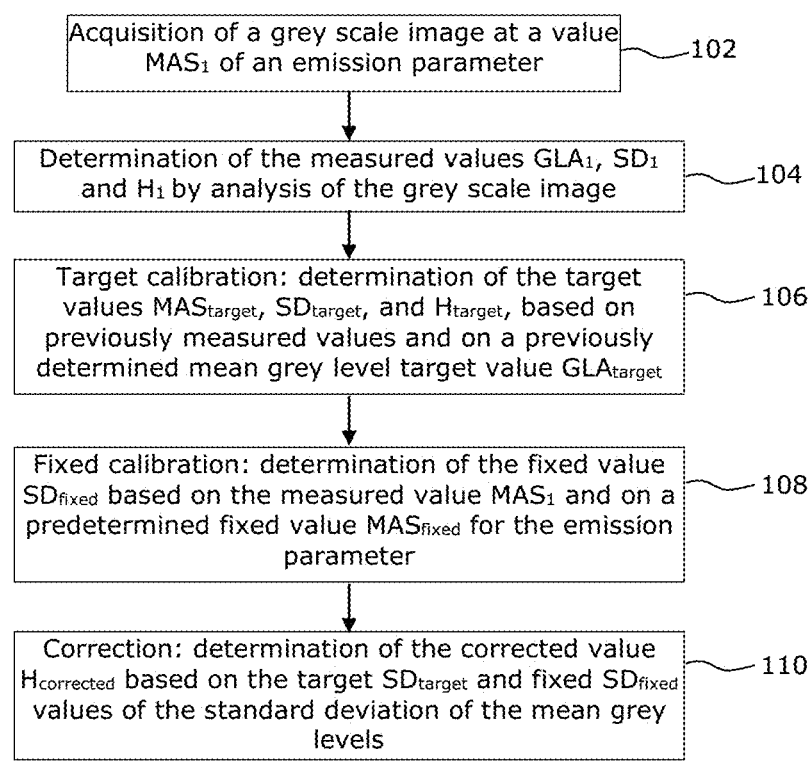
FIG. 1 is a diagrammatic representation of the steps of an example characterization method according to the invention.

FIG. 1 is a diagrammatic representation of the steps of an example imaging method according to the invention for imaging the calcaneum utilizing a radiation sensor trade marked Hamamatsu® offering 4096 grey levels.

In the present example, the characterization parameter the value of which is sought is the Hurst parameter H. The emission parameter is the dose of photons delivered by the emitter, in mAs. Hereinafter, this parameter will be denoted MAS.

The method 100 shown in FIG. 1 comprises a first step 102 of acquisition of a grey scale image with a value of $MAS_1 = 15$ mAs.

In step 104, the method 100 carries out the determination of a value, known as the measured value, for each of the following parameters by analysis of the grey scale image:

$GLA_1$: measured value of the mean grey level over the grey scale image;

$SD_1$: measured value of the standard deviation of the grey levels over the grey scale image; and $H_1$ determined as described above, i.e. as the derivative of the fractional Brownian motion determined by the maximum likelihood estimation method.

The method 100 also comprises a first step 106 of calibration, known as target calibration, carrying out a calibration of the measurement made with respect to a target value, $GLA_{target}$, of the mean grey level. This target value $GLA_{target}$ of the mean grey level is previously chosen for the sensor used for the acquisition of the grey scale image in step 102. In the context of this example, the sensor used is a radiation sensor trade marked Hamamatsu® offering 4096 grey levels. The chosen target value $GLA_{target}$ is 2000.

The step 106 of target calibration makes it possible to determine the target values with the following relationships:

$$SD_{target} = SD_1 \left( \frac{MAS_{target}}{MAS_1} \right) \quad (1)$$

$$MAS_{target} = MAS_1 \left( \frac{GLA_{target} - ct}{GLA_1 - ct} \right) \quad (2)$$

$$H_{target} = \quad (4)$$
$$H_1 + ((GLA_{target} - GLA_1) \cdot ((a \cdot 10^{-b}) - (c \cdot 10^{-d} \cdot (GLA_{target} + GLA_1))))$$

with "a", "b", "c", "d" and "ct" being constant values previously determined empirically for a given sensor, a bone tissue to be characterized. These values, which are specific to the detector model, can be determined by quadratic regression of H as a function of GLA on calibration phantoms the values of H and GLA of which are measured for different radiation doses (mAs).

This target calibration step, carried out with respect to the mean grey level, makes it possible to bring the measurement performed in step 102 into a usable range of grey levels recommended for the sensor used, and thus allowing it to be rendered independent of the measurement ranges used by one and the same sensor. Consequently, the target calibration makes it possible to eliminate measurement errors that may be caused by a measurement which may be offset in one direction or the other with respect to a measurement range optimized for the sensor.

The method 100 also comprises a first step 108 of calibration, known as fixed calibration, carrying out a calibration of the measurement made with respect to a fixed value, $MAS_{fixed}$, of the emission parameter, i.e. of the quantity of particles emitted in order to carry out the acquisition of the image. This fixed value $MASd_{fixed}$ of the emission parameter is previously chosen close to the lower limit of the emission parameter values observed in clinical imaging for a given sensor model. Within the context of this example, the sensor used is a radiation sensor trade marked Hamamatsu® offering 4096 grey levels. The chosen fixed value $MAS_{fixed}$ is 10 mAs.

During this calibration step the fixed value $SD_{fixed}$ of the standard deviation of the grey levels is determined. This value $SD_{fixed}$ will then be used to correct the measured value $H_1$ of the Hurst parameter. The fixed value $SD_{fixed}$ is determined according to the following relationship:

$$SD_{fixed} = SD_1 \left( \frac{MAS_{fixed}}{MAS_1} \right) \quad (3)$$

This fixed calibration step, carried out with respect to the emission parameter, makes it possible to bring the measurement carried out during step 102 to a fixed illumination condition of the bone tissue to be imaged, and thus to render the measurement performed independent of the illumination conditions used for the measurement.

The method 100 shown in FIG. 1 then comprises a step 110 of correction of the measured value $H_1$ of the characterization parameter, which in the present example is the Hurst parameter.

The correction step 110 makes it possible to determine the corrected value $H_{corrected}$ with the following relationship:

$$H_{corrected} = H_{target} + e\left(\frac{1}{SD_{fixed}} - \frac{1}{SD_{target}}\right) \quad (5)$$

with "e" being a constant.

Figure 2:
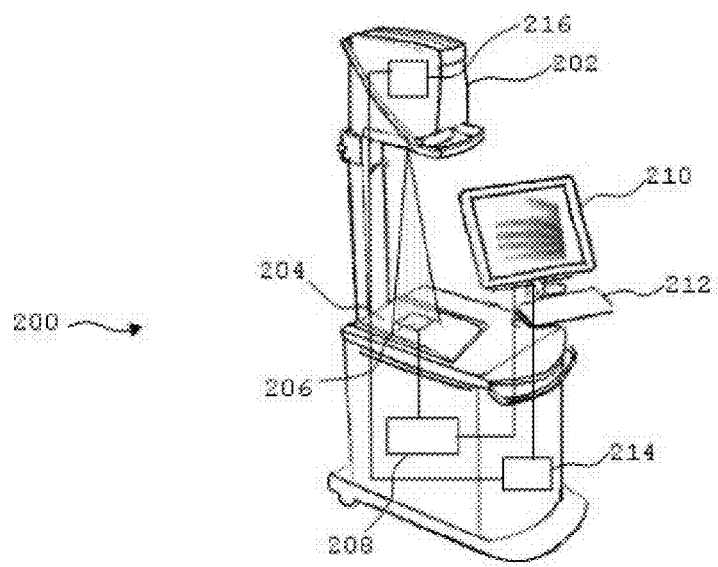
FIG. 2 is a diagrammatic representation of a system according to the invention.

FIG. 2 is a diagrammatic representation of an example of the imaging system 200 according to the invention.

The imaging system 200 is mobile. It comprises an emitter 202 of charged particle rays and a receiver 204 equipped with a sensor 206.

The sensor 206 is linked to a grey scale image generation module 208. The images generated by the image generation module 208 are displayed on a display screen 210.

The system 200 also comprises means 212 for selecting a region of interest on the image displayed on the display screen 210.

The system 200 comprises in addition a calculation module 214 for calculating the mean value of the grey levels in the images produced as well as the value of the standard deviation of the grey levels, the value of at least one characterization parameter, and the value of an emission parameter as a function of pre-set relationships.

The value of the emission parameter is provided to a control module 216 which makes it possible to modify and adjust the value of this parameter at the emitter 202.

Figure 3A:
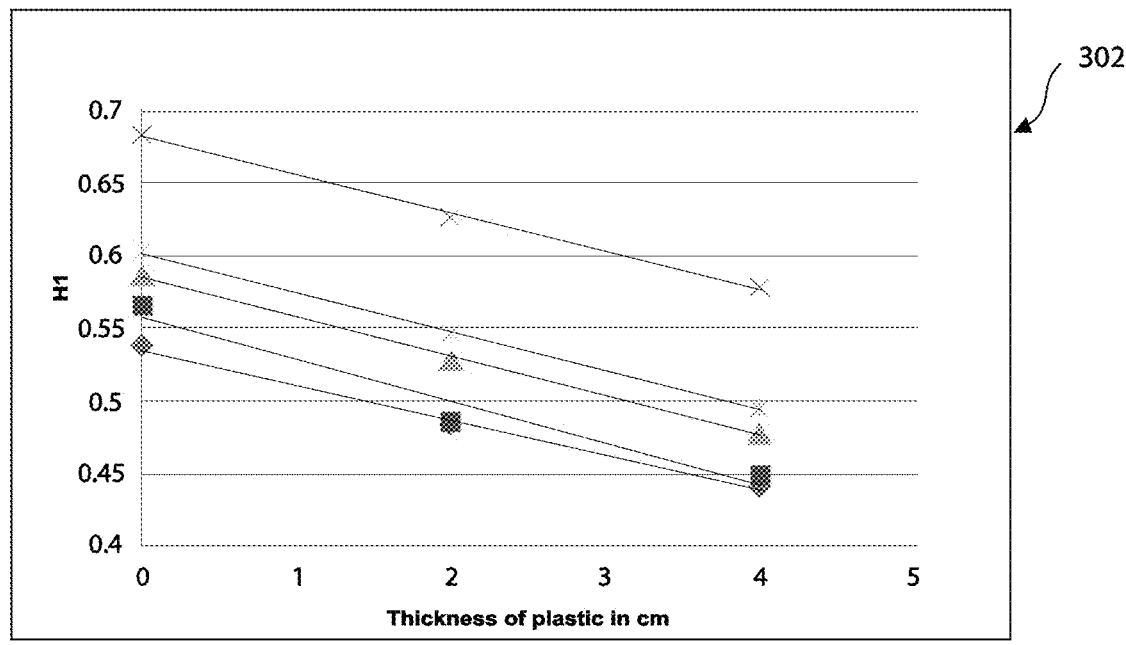
FIG. 3 is a diagrammatic representation of the results obtained with the method and system according to the invention.
Figure 3B:
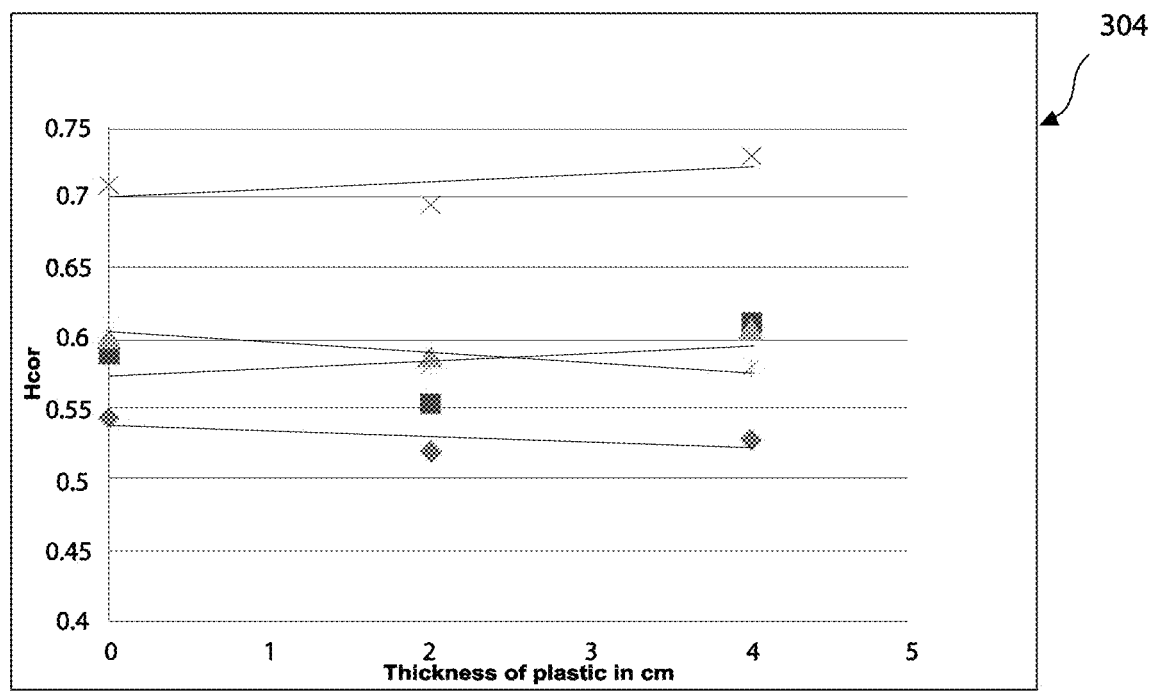

FIG. 3 is a diagrammatic representation of a non-limitative example of results obtained with the method and system according to the invention.

The curves 302 show the value $H_1$, of the parameter H measured for different emission doses and for a variable thickness of a plastic layer placed between the emitter and the bone tissue to be characterized. This plastic layer introduces stray radiation, captured by the detector and present in the grey scale image, the quantity of which depends directly on the thickness of the plastic layer.

The curves 304 show for each configuration the value $H_{cor}$ of the parameter H corrected according to the invention. On the given curves, the horizontal axis represents the thickness of the plastic layer in cm and the vertical axis the value of the parameter H, namely, the measured value $H_1$ for the curves 302 and the corrected value $H_{cor}$ for the curves 304.

The curves 302 clearly show that the measured value $H_1$ measured for one and the same bone tissue is not constant and decreases when the thickness of the plastic layer, placed between the bone tissue and the emitter, increases. This variation of the measured value $H_1$ is caused by the scattered radiation generated by the plastic layer and the dose used. In comparison, on the curves 304, the corrected value $H_{cor}$ of the parameter H is substantially constant, and no longer depends on the thickness of the plastic layer used, or the emitted dose used.

Of course, the invention is not limited to the examples that have just been described.

The invention claimed is:

1. A method implemented by a processor for the characterization of a bone tissue with an imaging device comprising a radiation emitter and utilizing a radiation sensor, said method comprising the following steps:
    acquiring at least one grey scale image of said bone tissue with said imaging device at a measurement value $MAS_1$ of an emission parameter relating to the emitted radiation,
    measuring, by analysis of said image:
        a measured value $SD_1$ of a standard deviation of the grey levels;
        a measured value $GLA_1$ of a mean grey level; and
        a measured value $H_1$ of a characterization parameter of said bone tissue;
    calibrating, in a target calibration step, said measured value $H_1$ of the characterization parameter with respect to a target value $GLA_{target}$ of a predetermined mean grey level for said sensor, said calibration producing a target value $H_{target}$ of said characterization parameter;
    calibrating, in a fixed calibration step, said measured value $SD_1$ of the standard deviation of the grey levels with respect to a fixed value $MAS_{fixed}$ of the predetermined emission parameter, said fixed calibration step producing a fixed value $SD_{fixed}$ of the standard deviation of the grey levels; and
    correcting the measured value $H_1$ of the characterization parameter according to the following relationship:

$$H_{corrected} = H_{target} + e\left(\frac{1}{SD_{fixed}} - \frac{1}{SD_{target}}\right)$$

with:
    $H_{corrected}$ is the corrected value of the parameter H1,
    $H_{target}$ is the target value of the parameter H1,
    $SD_{target}$ is the target value of the grey level standard deviation,
    $SD_{fixed}$ is the fixed value of the standard deviation of the grey levels, and
    e is a constant value,
    wherein in order to obtain a corrected value $H_{corrected}$, known as a corrected value of the value of said characterization parameter $H_1$, said corrected value $H_{corrected}$ is a function of said target value $H_{target}$ of said characterization parameter $H_1$,
    wherein the target value ($H_{target}$) of the characterization parameter is determined according to the following relationship:

$$H_{target} = H_1 + ((GLA_{target} - GLA_1) \cdot ((a \cdot 10^{-b}) - (c \cdot 10^{-d} \cdot (GLA_{target} + GLA_1))))$$

with:
    $H_{target}$ is the target value of the parameter $H_1$,
    $H_1$ is the measured value of the parameter $H_1$,
    $GLA_{target}$ is the mean grey level target value,
    $GLA_1$ is the mean grey level measured value, and
    α, b, c and d, are constant values determined empirically, and
    wherein the characterization parameter H is a characterization parameter of the bone tissue, also known as the Hurst parameter.

2. The method of claim 1, wherein the target calibration step comprises determining the target value of the standard deviation of the grey levels as a function of the measurement value $MAS_1$ of the emission parameter and of a predetermined target value $MAS_{target}$ of said emission parameter.

3. The method of claim 2, wherein the target calibration step also comprises determining the target value $MAS_{target}$ of the emission parameter as a function of the measurement value of the emission parameter $MAS_1$, of the measured value $GLA_1$ of the mean grey level, and of the predetermined grey level target value $GLA_{target}$ for the sensor used.

4. The method of claim 1, wherein the image is acquired around a region of interest, previously identified on the image, by at least one anatomical marker.

5. The method of claim 1, wherein the fixed value $SD_{fixed}$ of the standard deviation of the grey levels is determined according to the following relationship:

$$SD_{fixed} = SD_1\left(\frac{MAS_{fixed}}{MAS_1}\right).$$

6. The method of claim 2, wherein the target value $SD_{target}$ of the standard deviation of the grey levels is determined according to the following relationship:

$$SD_{target} = SD_1\left(\frac{MAS_{target}}{MAS_1}\right).$$

7. The method of claim 3, wherein the target value $MAS_{target}$ of the emission parameter is determined according to the following relationship:

$$MAS_{target} = MAS_1\left(\frac{GLA_{target} - ct}{GLA_1 - ct}\right)$$

wherein ct is a constant value.

8. The method of claim 7, wherein at least one constant value is a value previously determined empirically for a given sensor and for a given characterization parameter.

9. The method of claim 1, comprising the characterization of bone tissues of a part of the body of a living organism.

* * * * *